(12) United States Patent
Higuchi (10) Patent No.: US 6,358,470 B1
(45) Date of Patent: Mar. 19, 2002

(54) AUTOMATIC DISTRIBUTION APPARATUS FOR INSERTING NOZZLES INTO TIPS

(75) Inventor: Akira Higuchi, Fukuoka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/414,723

(22) Filed: Oct. 8, 1999

(30) Foreign Application Priority Data

Oct. 12, 1998 (JP) .......................................... 10-289105

(51) Int. Cl.⁷ ................................................ B01L 9/00
(52) U.S. Cl. .................... 422/63; 73/864.14; 73/864.17; 422/100; 422/104; 436/180
(58) Field of Search .............................. 422/63, 65, 67, 422/68.1, 99, 100, 104; 436/47, 180; 73/863.23, 864.01, 864.02, 864.25, 864.13, 864.14, 864.16, 864.17

(56) References Cited

U.S. PATENT DOCUMENTS

| | | | | |
|---|---|---|---|---|
| 4,478,094 A | * | 10/1984 | Salomaa et al. .............. | 422/65 |
| 5,102,623 A | * | 4/1992 | Yamamoto et al. ........... | 422/63 |
| 5,497,670 A | * | 3/1996 | Carl ........................ | 73/864.14 |
| 6,116,099 A | * | 9/2000 | Carl ........................ | 73/863.32 |
| 6,238,626 B1 | * | 5/2001 | Higuchi et al. ............. | 422/100 |

* cited by examiner

Primary Examiner—Joseph W. Drodge
(74) Attorney, Agent, or Firm—Wenderoth, Lind & Ponack, L.L.P.

(57) ABSTRACT

A distribution head 14 is provided with nozzles 17. A tip holder 5 is placed on a platform 53 which is supported on a rod 52 of a cylinder 51. The tip holder 5 holds a number of distribution tips 15 upright. The nozzles 17 are fitted to the top portion of the distribution tips 15 by lowering the distribution head 14. As the platform 53 is elastically supported on the rod 52 of cylinder 51 so that it can move slightly up and down, the distribution tips 15 may be surely fitted to the nozzles 17 without suffering from damage. Air pressure given to the cylinder 51 is adjusted in accordance with the total number of tips 15, or other factors.

9 Claims, 13 Drawing Sheets

AUTOMATIC DISTRIBUTION APPARATUS FOR INSERTING NOZZLES INTO TIPS

FIELD OF THE INVENTION

The present invention relates to an automatic distribution apparatus for distributing medical liquid, specimens and other samples in liquid state.

BACKGROUND OF THE INVENTION

In the field of activities where systematic experimental studies about technical reactions of various kinds of materials, for example, are conducted, the automatic distribution apparatus is one of the indispensable facilities. The automatic distribution apparatus automatically performs various operations, for example, taking samples of liquid medicine, etc. out of a plate, or a sample keeping body for keeping the samples and transferring them to other places. The plate is provided with a number of small hollows disposed in a lattice form for storing liquid samples. The elementary action in the distributing operations is sucking up the sample liquids kept in the hollows using distribution tips attached to a distribution head, and discharging them. The distribution tips are replaced with new ones each time the sample liquid is changed to another kind, or at every distributing operation.

There may be two modes in the distributing operation: a case where all of each sample liquid kept in the total hollows of a plate are distributed altogether by a distribution head at once; and a case where only the liquid samples kept in certain specific hollows are distributed. Therefore, the distribution head comes in various configurations: one having a number of distribution tips disposed in a lattice form that corresponds to the arrangement of hollows of a plate; and the other having the distribution tips corresponding to a certain specific row of the hollows of a plate, or in other different tip arrangements. At each distribution operation, a suitable distribution head is selected in accordance with specific objectives of the operation.

It is required that the distribution tips can be replaced within a short period of time. To attain this objective, fitting of the distribution tips to all of the nozzles of a distribution head should be done in one operation. As described earlier, some of the distribution heads must be fitted with distribution tips in a lattice arrangement while other distribution heads require the distribution tips in a line arrangement. In distribution heads of different types that require the distribution tips in different numbers and arrangement, it is essential that the distribution tips be fitted surely and quickly. Because the distribution tips are made of a resin or other such physically weak material to take a long tubular shape, it is also required to pay utmost care not to cause damage to a distribution tip during fitting.

SUMMARY OF THE INVENTION

The present invention aims to offer an automatic distribution apparatus in which the distribution tips can be fitted to a distribution head quickly and surely.

The automatic distribution apparatus comprises a distribution head provided with a plurality of nozzles each having a tip for sucking liquid sample at the bottom end, a tip exchange stage on which a tip holder holding a plurality of unused tips upright is placed, and moving means for moving the distribution head up and down relative to the tip holder placed on the tip exchange stage for the purpose of having the bottom ends of the nozzles inserted in the tips held in the tip holder. The tip exchange stage is equipped with a platform for holding a tip holder, thrusting means for thrusting the platform upward, and control means for controlling the thrusting force.

With the above-described structure, where the tip holder is thrust upward by the thrusting means and the thrusting force is controlled to an appropriate level, any predetermined number of distribution tips can be fitted to a distribution head automatically in one operation with high reliability, and a possible breakage of a distribution tip during the fitting action can also be avoided.

It is preferred that the control means can change the thrusting force depending on a number, and a type, of the distribution tips to be fitted at each one operation. Controlling the thrusting force of the thrusting means in accordance with such factors as the number of tips to be fitted to provides the distribution tips with an appropriate cushion power to ensure the fitting at a high certainty.

It is also preferred that an air cylinder is used for the thrusting means, and an air pressure regulator is used for the control means.

DESCRIPTION OF THE PREFERRED EMBODIMENT

Figure 1:
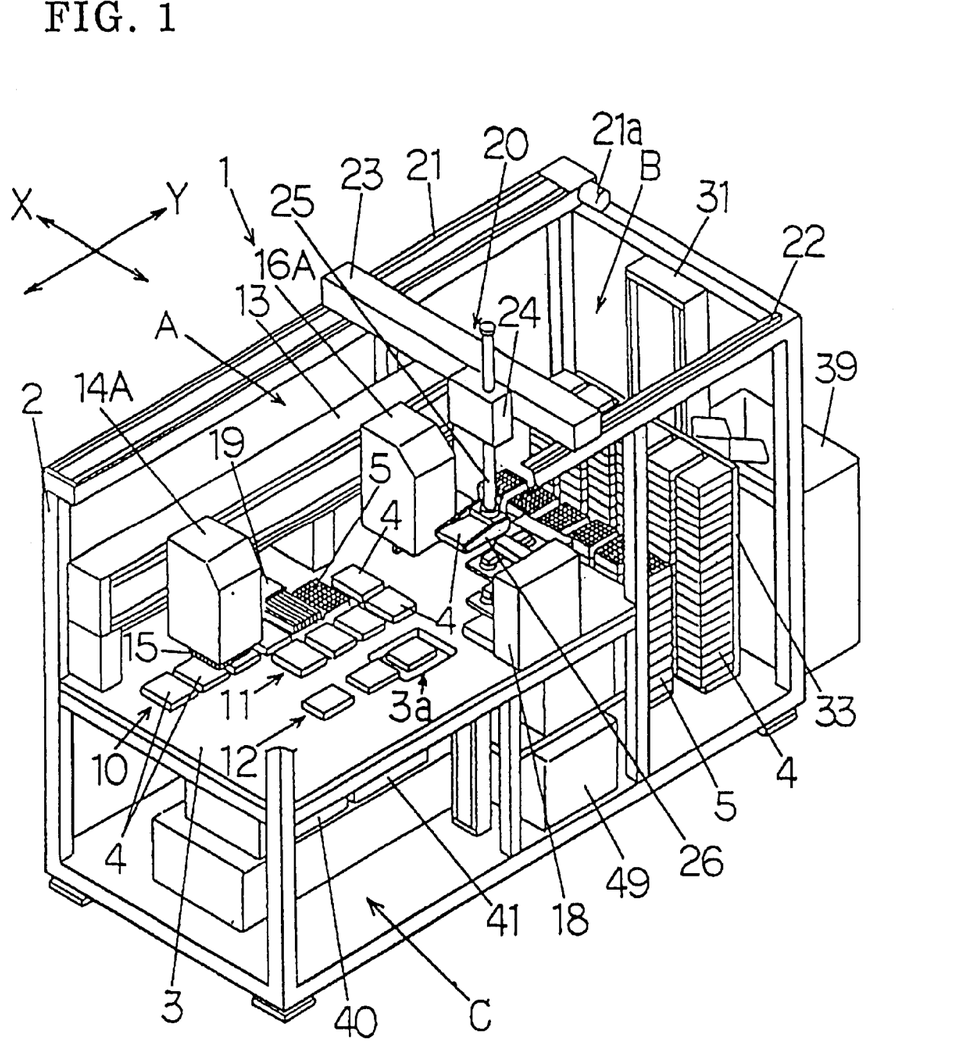
FIG. 1 shows a perspective view of an automatic distribution apparatus in accordance with an exemplary embodiment of the present invention.

Overall structure of an automatic distribution apparatus is described with reference to FIG. 1. In FIG. 1, automatic distribution apparatus 1 comprises a frame 2 formed of a combination of metal members and a base plate 3 mounted and fixed on the frame 2. The automatic distribution apparatus 1 may be divided by the frame 2 and the base plate 3 into three sections: a distribution section A, a stock section B and a processing section C. The distribution section A is disposed on the base plate 3, which section performs distributing of samples to a plate, or sample keeping body. The stock section B stocks plates and distribution tips to be used in the distribution section A. The processing section C is a section for analyzing and cleaning the plates that carried distributed samples to an incubator or other such facilities and returned.

Now the internal structures will be described with reference to FIG. 1 through FIG. 14. In the distribution section A, provided on the base plate 3 are three stages for placing the plates 4 on, namely, a distribution stage 10, a buffer stage 11 and a waiting stage 12. On the distribution stage 10, a plate 4 is placed for distribution of medicines or other sample liquids. The buffer stage 11 plays a role of a buffer in temporarily keeping the plate 4. The waiting stage 12 is a space provided on the base plate 3 for the plate 4 waiting for a turn to be sent through an opening 3a to the processing section C located underneath.

Provided at a side of the distribution stage 10 is a transfer table 13, which is disposed along the length direction of the distribution stage 10. Provided on the transfer table 13 are a box 14A containing a first distribution head 14 (ref FIG. 2A) and a box 16A containing a second distribution head 16 (ref FIG. 2B). Each of the first distribution head 14 and the second distribution head 16 can move independently, driven by respective moving means (not shown), in the Y direction along the transfer table 13 on the distribution stage 10. Namely, the distribution stage 10 provides a common field for the operation of the first distribution head 14 and the second distribution head 16. The first and the second distribution heads 14, 16 are provided respectively with nozzles 17 on their bottoms, and each of the nozzles 17 can freely be fitted with, and detached from, a distribution tip 15 (ref FIG. 10). The box 14A is eliminated in the illustrations of FIG. 11 through FIG. 13.

Figure 2A:
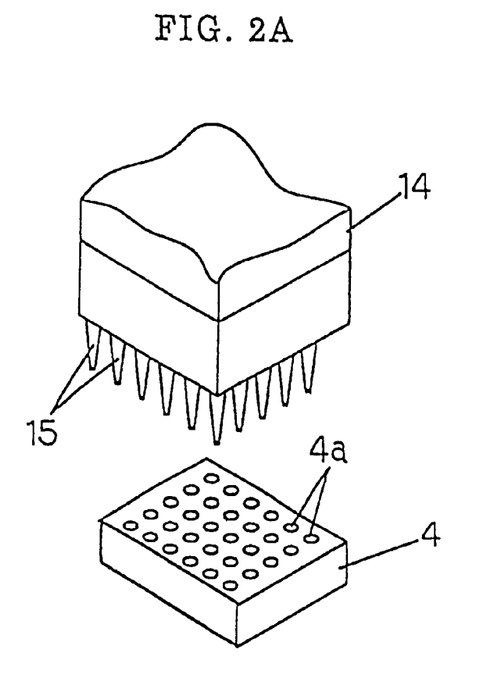
FIG. 2A is a perspective view showing part of a distribution head having a lattice arrangement, in the above distribution apparatus.
Figure 2B:
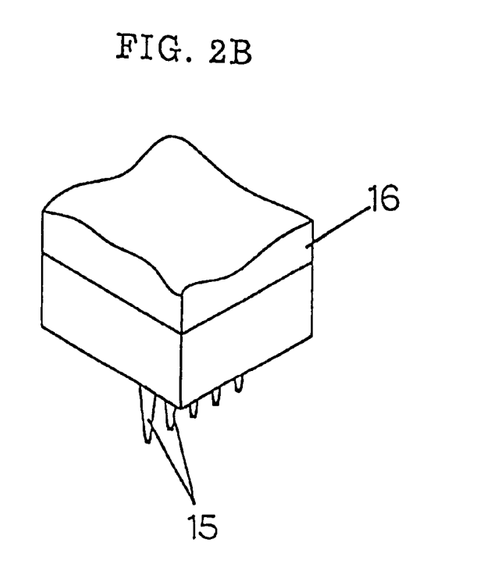
FIG. 2B is a perspective view showing part of a distribution head having a single line arrangement, in the above distribution apparatus.

The distribution tip 15 is a nozzle component having a tapered shape that is fitted to and detached from the bottom end of the distribution nozzle 17; namely, it is a disposable component. As shown in FIG. 2A, the first distribution head 14 is provided with a plurality of distribution tips 15 arranged in a lattice form (in the present exemplary case, 6 pcs×5 rows=30 pcs), whereas the second distribution head 16 has the distribution tips 15 for one row (in the present exemplary case, 6 pcs). The first distribution head 14 is provided with 30 nozzles, and the second distribution head 16 is provided with the nozzles for 6 pcs, a number smaller than that of the first distribution head.

Transfer, distribution or other such operations with liquid samples are conducted by first lowering a tip-end of the distribution tip 15 into a hollow 4a provided in the lattice form on a plate 4 to suck up the medical liquid or other such sample liquid kept therein, and then discharging it in a hollow 4a of another plate 4. Use of the first distribution head 14 enables distribution of all of the sample liquids kept in the respective hollows 4a of plate 4 together in one operation. Use of the second distribution head 16 enables selective distribution, which is a distribution of only those liquid samples kept in the hollows 4a of any specific row.

Figure 7A:
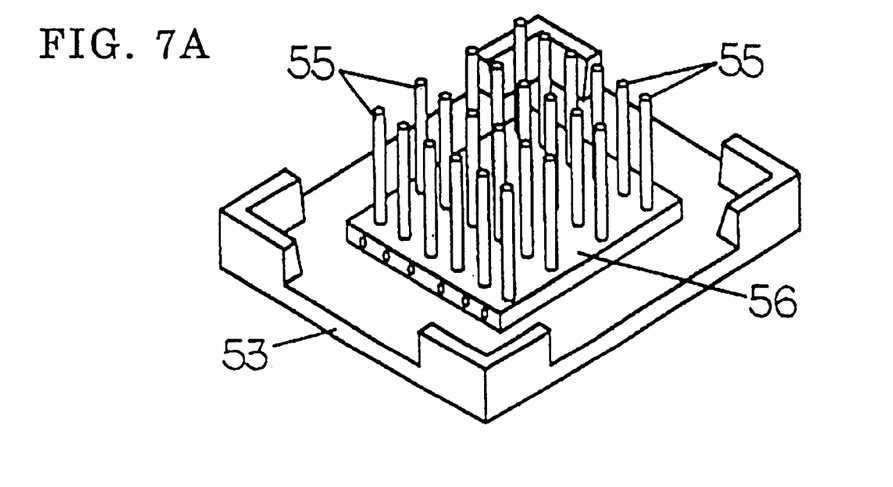
FIG. 7A is a perspective view of a holding section of the apparatus.
Figure 7B:
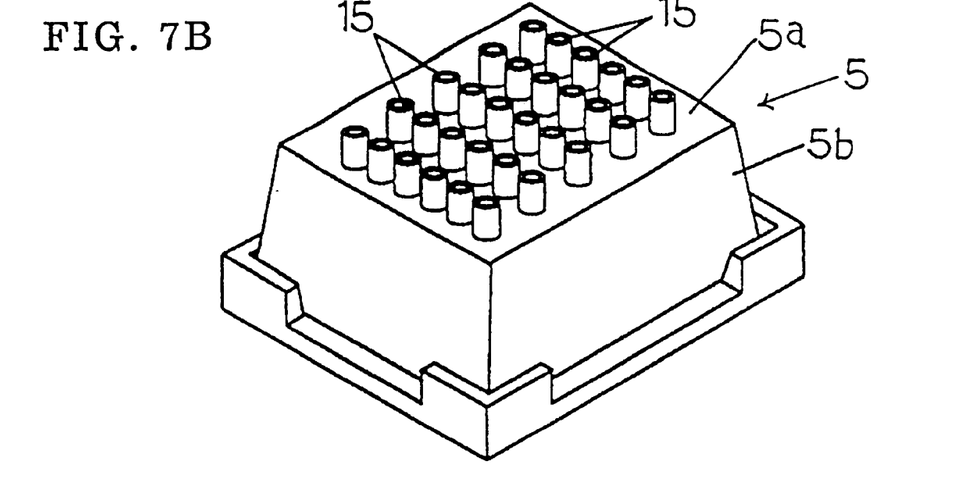
FIG. 7B is a perspective view of the holding section with a tip holder placed thereon.

The distribution tips 15 are supported in a tip holder 5 as shown in FIG. 7B, the tip holder 5 being a bottomless box for holding the distribution tips 15 in the same lattice arrangement as the hollows 4a. The tip holder 5 is formed of a top board 5a and feet portions 5b extending downward from the top board 5a; the top board 5a is provided with a number of holes for insertion of the tips in the same arrangement corresponding to that of the nozzles 17 of the first distribution head 14. Therefore, lowering of the distribution head 14, 16 onto the tip holder 5, after making a precise alignment of their relative positions, automatically brings about a forced elastic fitting of the distribution tips 15 to respective nozzles 17 of the distribution head 14, 16. After a distributing operation is finished, the distribution tips 15 are automatically detached from the distribution head 14, 16 by moving the distribution head 14, 16 up and down above a tip detaching mechanism 19 provided in the distribution section A (ref FIG. 1); a combed plate of the mechanism hooks the distribution tips 15 down. An uncovering unit 18 is provided on the transfer table 13 at the opposite end. The uncovering unit 18 is for removing the cover of plate 4 while the plate 4 is stored in the stock position.

Next, the stock section B is described with reference to FIG. 3 and FIG. 4. A plate stocker 30 is provided in the stock section B. A Z-axis table 31 equipped with a motor 31a is mounted and fixed on the frame 2. A back plate 33 is provided on a slider of the Z-axis table 31. The back plate 33 has a plurality of shelf boards 34 disposed in a plurality of rows, which shelf board is for placing a plate 4 thereon.

Each of the rows of the shelf boards is specified for a particular kind of a plate 4. As illustrated in FIG. 4, the shelf board rows 34A, 34B are for dilution plates 4A, which keep dilution solution, the shelf board rows 34C, 34D are for medicine plates 4B, which keep medical liquid, and the shelf board rows 34E, 34F are for specimen plates 4C, which keep liquid specimen. Driving the motor 31a brings any specific plate 4 stored on the shelf board 34 up or down to a height at which a transfer head 26 (ref FIG. 1 and FIG. 8) can clamp it.

A tip stocker 35 is provided opposite to the plate stocker 30, such that the two stockers face each other. The tip stocker 35 is structured of a stock table 37 which is provided on a Z-axis table 36 disposed vertically and containing a motor 36a. On the stock table 37, tip holders 5 holding unused distribution tips 15 are stacked in layers. Moving the Z-axis table 36 brings a tip holder 5 among those stacked up or down to a height at which the transfer head 26 can clamp it.

Next, a ceiling transportation gear 20, or transfer means, is described with reference to FIG. 1. The ceiling transportation gear 20 is structured of a Y-axis table 21, an X-axis table 23, an elevation/revolution unit 24 and the transfer head 26. The Y-axis table 21 is disposed on the frame 2 along the direction of the length, the X-axis table 23 is driven at one end by the Y-axis table 21 and the other end is supported by a guide rail 22 provided on the frame 2. The elevation/revolution unit 24 is driven by the X-axis table 23, and the transfer head 26 is disposed at the bottom end of an arm 25, which is hanging from the elevation/revolution unit 24.

The ceiling transportation gear 20 takes part of intersectional transfer of plates 4 and tip holders 5 between the distribution section A and the stock section B, or between the distribution section A and other facilities. Namely, the transfer head 26 clamps a plate 4 on shelf board 34 of the plate stocker 30, and a tip holder 5 on stock table 37 of the tip stocker 35, for transfer and placement at a certain specified position.

Figure 3:
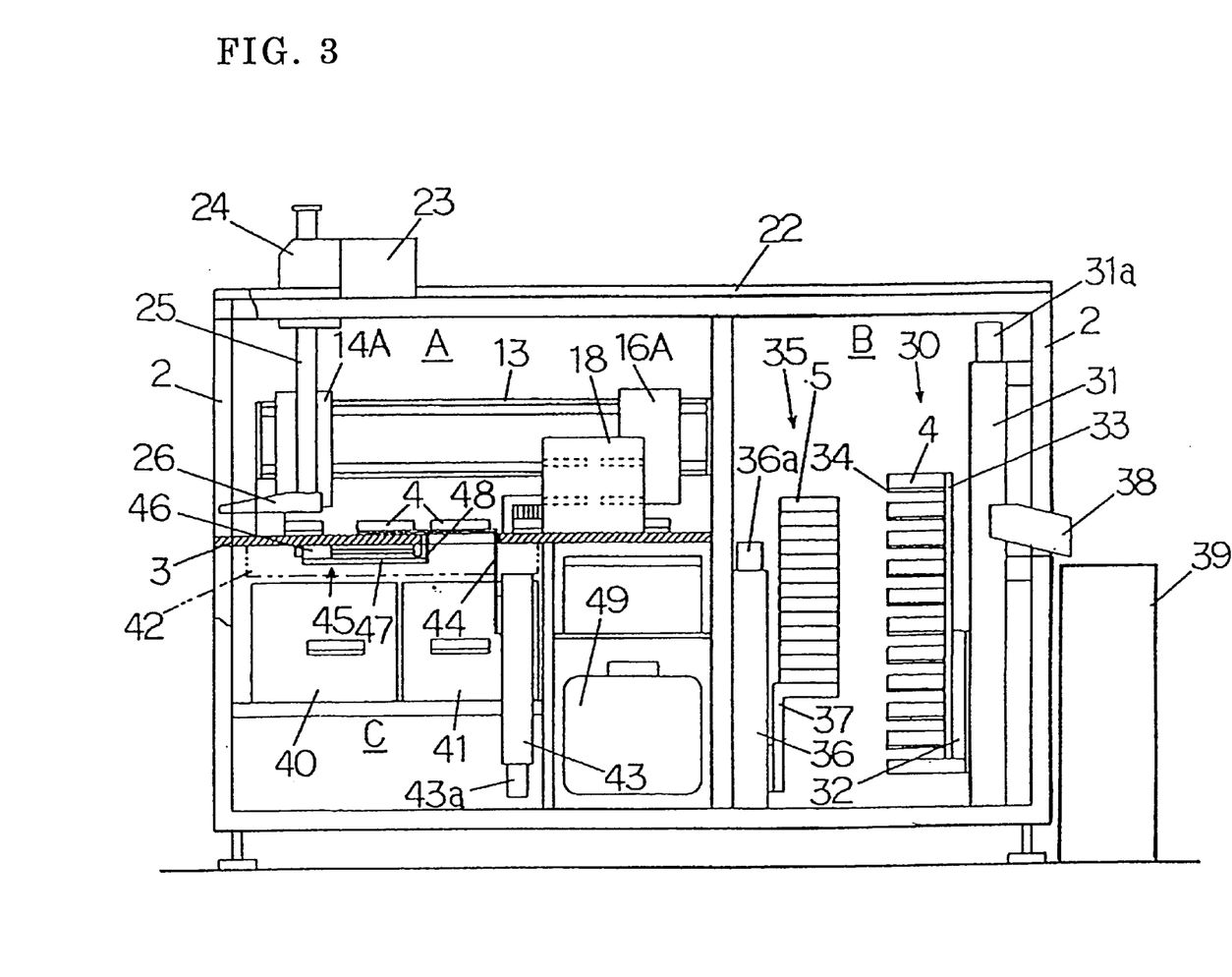
FIG. 3 is a front view of the automatic distribution apparatus.
Figure 4:
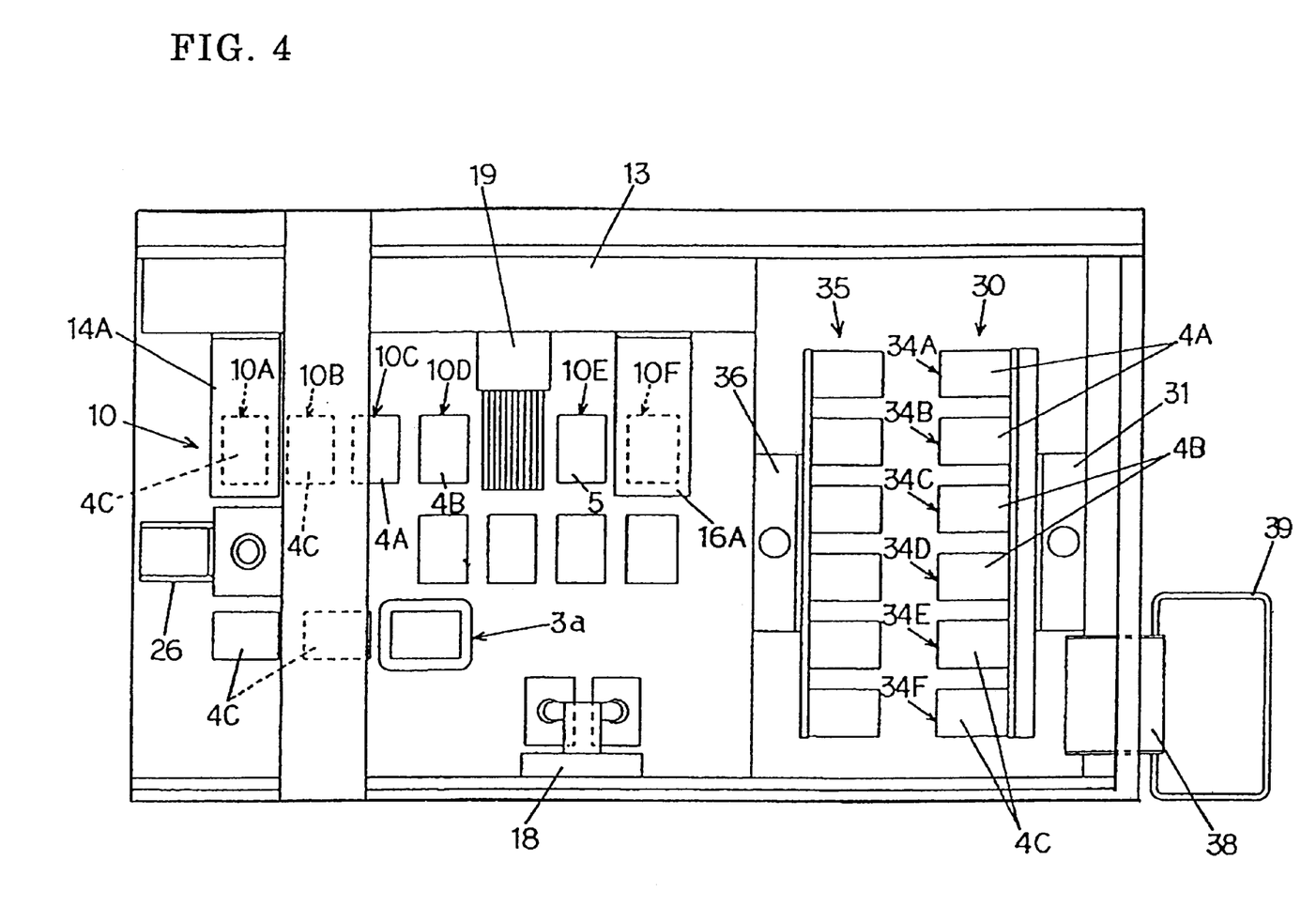
FIG. 4 is a plan view of the automatic distribution apparatus.

Description of the processing section C follows, with reference to FIG. 3. An analyzer 40 and a cleaner 41 are provided underneath the base plate 3. The analyzer 40 measures and analyzes the samples kept on a plate 4. The cleaner 41 cleans the plate 4 after the measurement and analysis are finished. Provided at a side of the cleaner 41 is a tank 49 for waste liquids. The tank 49 stores waste waters used for cleaning in the cleaner 41, which water originally came from a separate tank of processed water (not shown).

Figure 5:
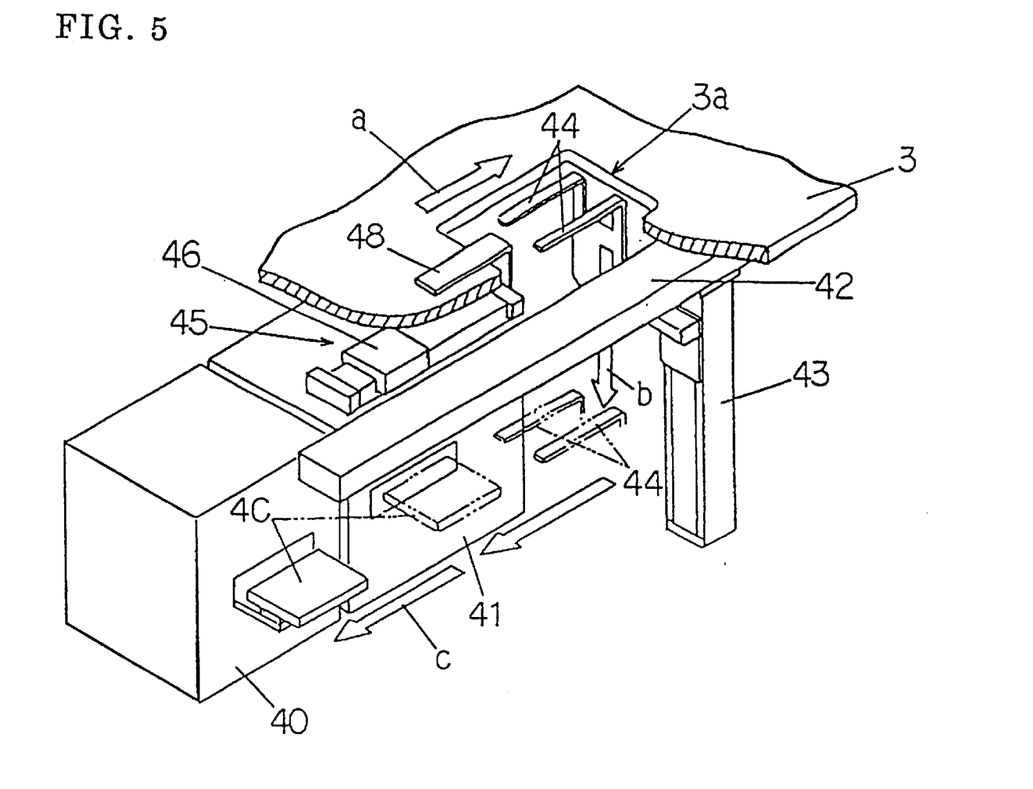
FIG. 5 is a perspective view of transfer means in the distribution apparatus.

Next, second transfer means for transferring a plate 4 between the distribution section A and the processing section C will be described, referring to FIG. 3 and FIG. 5. At a place below the base plate 3 and outside the opening 3a, a Y-axis table 42 is provided. A Z-axis table 43 containing a motor 43a is attached vertically to the Y-axis table 42. The Z-axis table 43 is provided with a vertical transfer arm 44 formed of two claws shaped like a letter "L". The motor moves the vertical transfer arm 44 up and down. The vertical transfer arm 44 is located in the same place as the opening 3a, and transfers a plate 4 up and down in a direction parallel to the Z-axis table 43.

Underneath the base plate 3 is a slide unit 45 disposed in parallel to the Y-axis table 42. A slider 46 of the slide unit 45 is connected to a horizontal transfer arm 48 with a connecting material 47 interposing in between. The horizontal transfer arm 48 is extending through the opening 3a on the surface of base plate 3 for transferring a plate 4 in the horizontal direction. Moving the horizontal transfer arm 48, by driving the slide unit 45, to a space between the two claws of the vertical transfer arm 44 brings a plate 4 placed on the horizontal transfer arm 48 to a position above the vertical transfer arm 44. Then, retracting the slide unit 45 while the plate 4 is being supported by the elevated vertical transfer arm 44 puts the transferred plate 4 on the vertical transfer arm 44.

The plate 4 is lowered by the vertical transfer arm 44 driven by the motor 43a, and then it is carried to the analyzer 40 or the cleaner 41 by the action of the Y-axis table 42. A disposal box 39 is provided at a side portion of the stock section B. The used distribution tips 15 are restored in the tip holder 5, and they are carried by the ceiling transportation gear 20 to be dropped on a chute 38 for collection in the disposal box 39.

Next, stage layout of the distribution stage 10 is described with reference to FIG. 4. There are six stages 10A–10F, specified on the distribution stage 10. Each of the stages is designated for a specific kind of the plate 4. The stages 10A, 10B are for the specimen plates 4C, the stage 10C is for the dilution plates 4A, or sample keeping body, and the stage 10D is for the medicine plates 4B. The stage 10E is for the exchange of tips, on which a tip holder 5 is placed with the distribution tips 15 inserted thereon.

Figure 8:
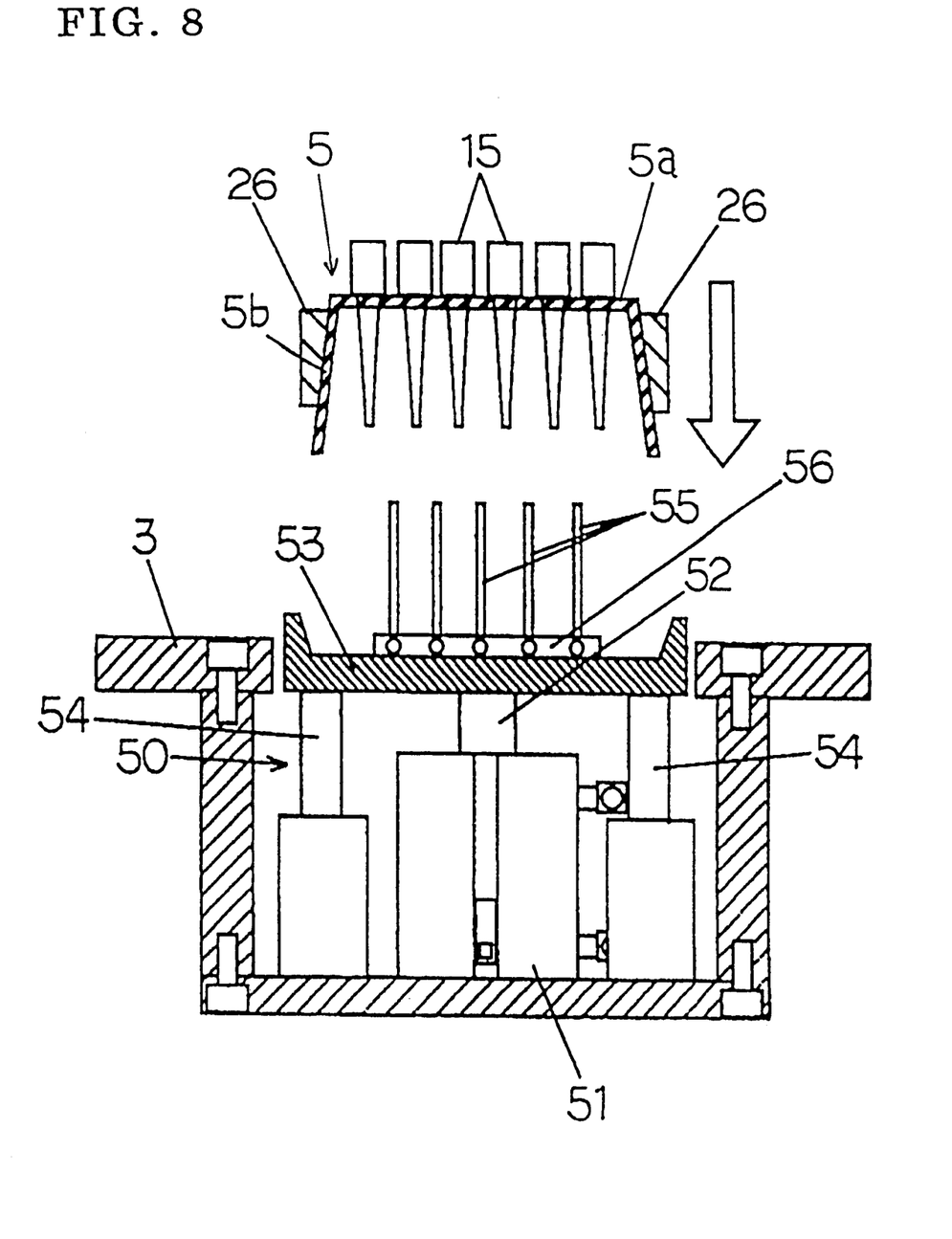
FIG. 8 through FIG. 13 are side views of a tip exchange stage of the distribution apparatus, which show a sequence of the operation.

Next, structure of the tip exchange stage 10E is described with reference to FIG. 8. A cylinder 51 is provided in a local recess 50 of the base plate 3. A rod 52 of the cylinder 51 supports a platform 53 having a plate form. The platform 53 moves up and down along guide rods 54 together with up and down action of the rod 52 of cylinder 51.

Figure 7C:
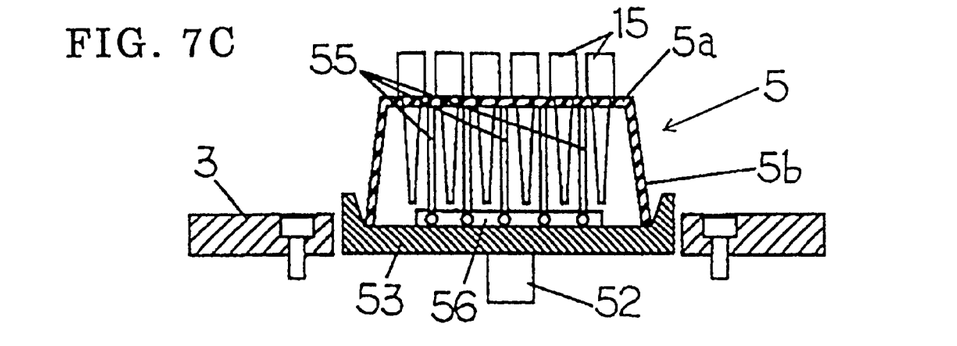
FIG. 7C is a cross sectional view of the holding section with a tip holder placed thereon.

Provided on the platform 53 is a pedestal 56 having a plurality of pin-like pillars 55 disposed upright thereon (ref FIG. 7A). A tip holder 5 is clamped by the transfer head 26 and transferred to the platform 53 (ref FIG. 7B, FIG. 7C). The pillars 55 make contact with the bottom surface of the top board 5a of tip holder 5 in order to prevent the flexible top board 5a from deforming downwardly. In order for the downward deformation to be as small as possible, it is preferred to provide plural pillars 55. The tip holder 5 is formed of a resin or other such flexible material.

Figure 14:
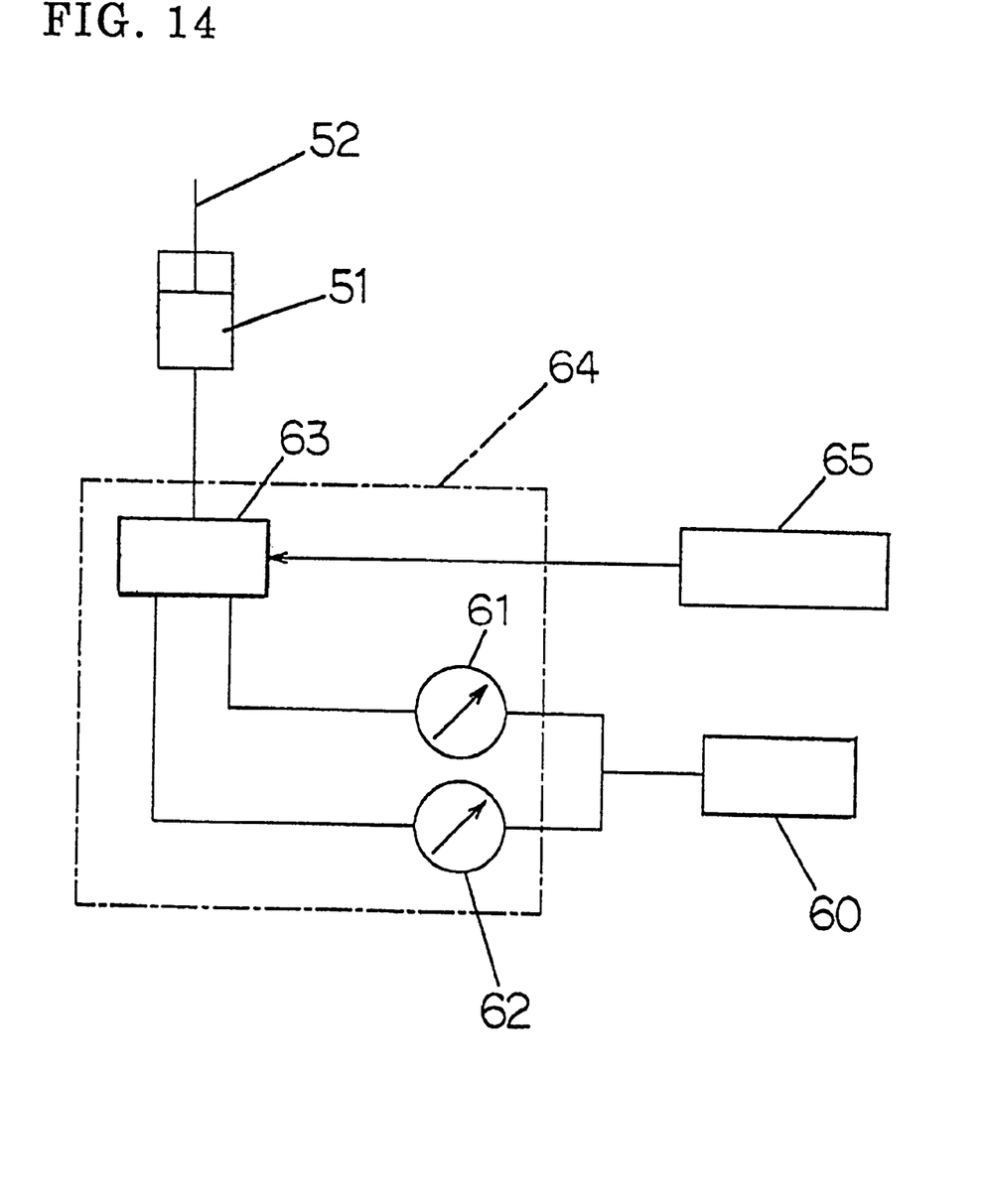
FIG. 14 shows a cylinder connection diagram in the distribution apparatus.

FIG. 14 shows a piping system for the cylinder 51. A pressure source 60 is connected with the cylinder 51 via a plurality (two, in the present exemplary case) of pressure regulators 61, 62 and a valve 63. The regulators 61, 62 and the valve 63 constitute pressure regulation means 64 for regulating the value of air pressure applied on the cylinder 51. The valve 63 is controlled by a control section 65.

Either one of the regulators 61 and 62 is put in use depending on a number of distribution tips 15 provided on a distribution head. In the present exemplary case, the regulator 61 is connected to the cylinder 51 when there are 6 distribution tips 15 on the distribution head, whereas the regulator 62 is connected to the cylinder 51 when there are 30 distribution tips 15 on the distribution head. Namely, in a case when the number of distribution tips 15 is small, a regulator 61 of smaller pressure is connected to the cylinder 51, being a thrust means for thrusting the tip holder 5 up and down from the bottom; while in a case when there are a great number of distribution tips 15, a regulator 62 of greater pressure is connected to the cylinder 51.

Although the number of tips remains the same, the thrusting force may be varied in accordance with the kind or the model of tips (distinguished by a plant where the tips are. manufactured, or the material, dimensions, etc. of the tips).

Figure 10:
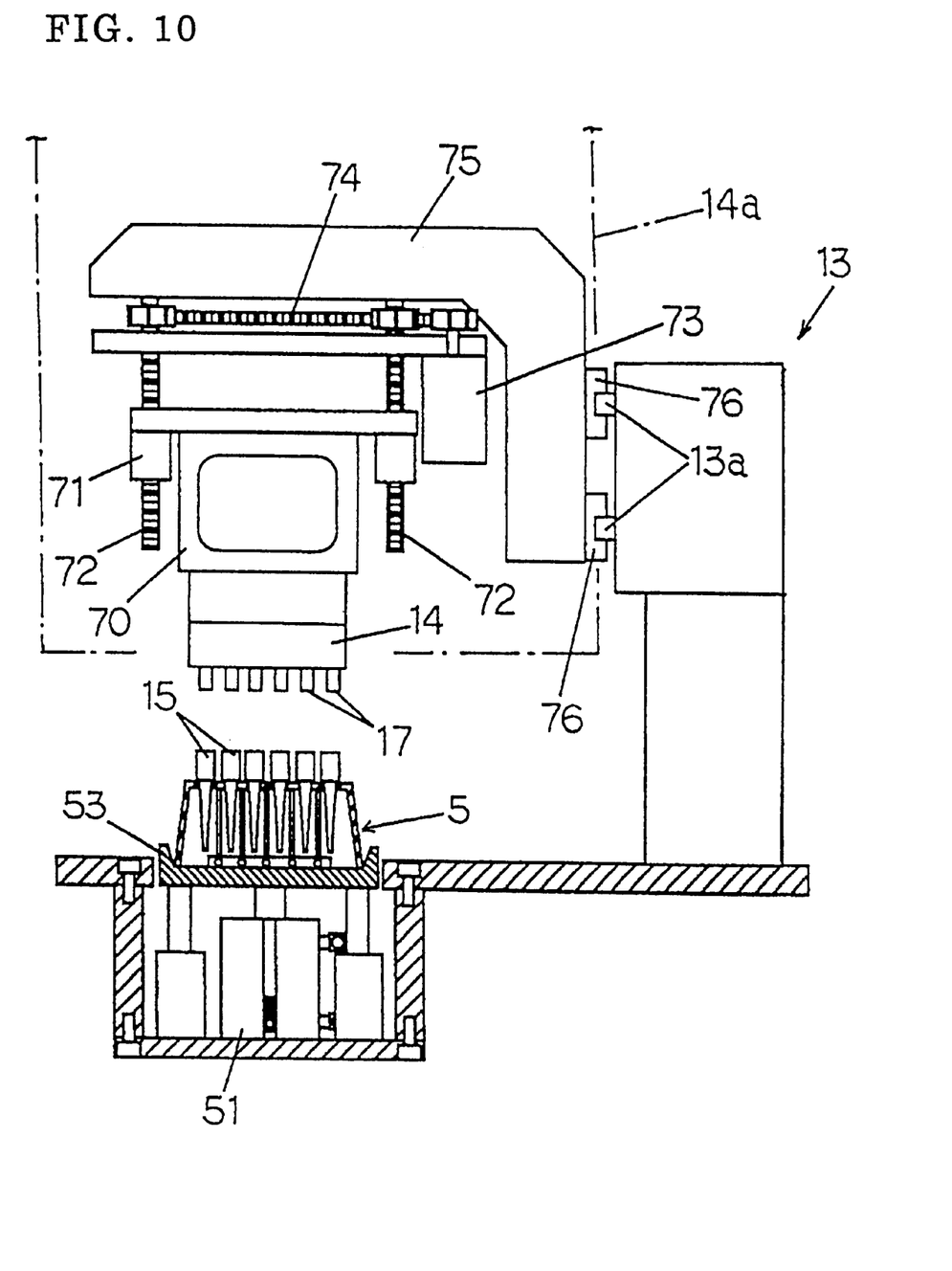

Now referring to FIG. 10, means for moving the distribution head up and down is described. A distribution head 14 is held by a holder 70. The holder 70 is provided with a nut 71 engaged with a vertical transfer screw 72. Revolving the transfer screw 72 with a motor 73 brings about an up and down motion of the nut 71 along the transfer screw 72. As the result, the distribution head 14 moves up and down relative to a tip holder 5 placed on the platform 53. A belt 74 is for conveying the revolution of motor 73 to the transfer screw 72. The nut 71, the transfer screw 72, the motor 73 and the belt 74 constitute means of up and down motion of the first distribution head 14 (first up-and-down means). Means of up and down motion having similar structure is provided also for the second distribution head (second up-and-down means).

The transfer screw 72 is mounted in an angle-shaped frame 75. A slider 76 on the back face of the frame 75 is supported in a free sliding manner by a guide rail 13a disposed horizontally in the front face of transfer table 13. FIG. 10 illustrates a supporting structure for the first distribution head 14; the second distribution head 16 is also supported by a similar structure.

Figure 9:
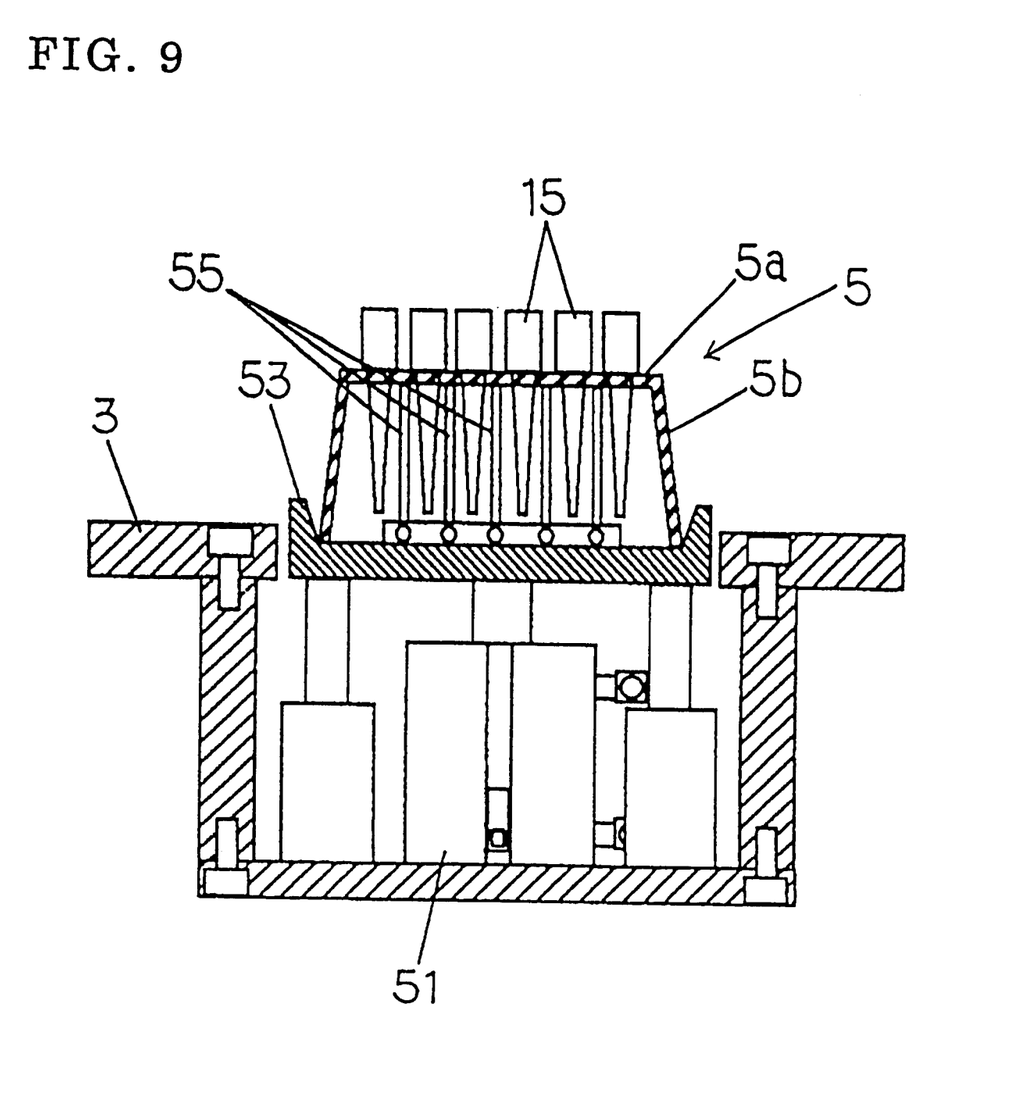

Operation of the above automatic distribution apparatus is described in the following. Referring to FIG. 3, a transfer head 26 transfers a tip holder 5 among those stored in a tip stocker 35 onto a platform 53 located in a tip exchange stage 10E (ref FIG. 8, FIG. 9).

Figure 11:
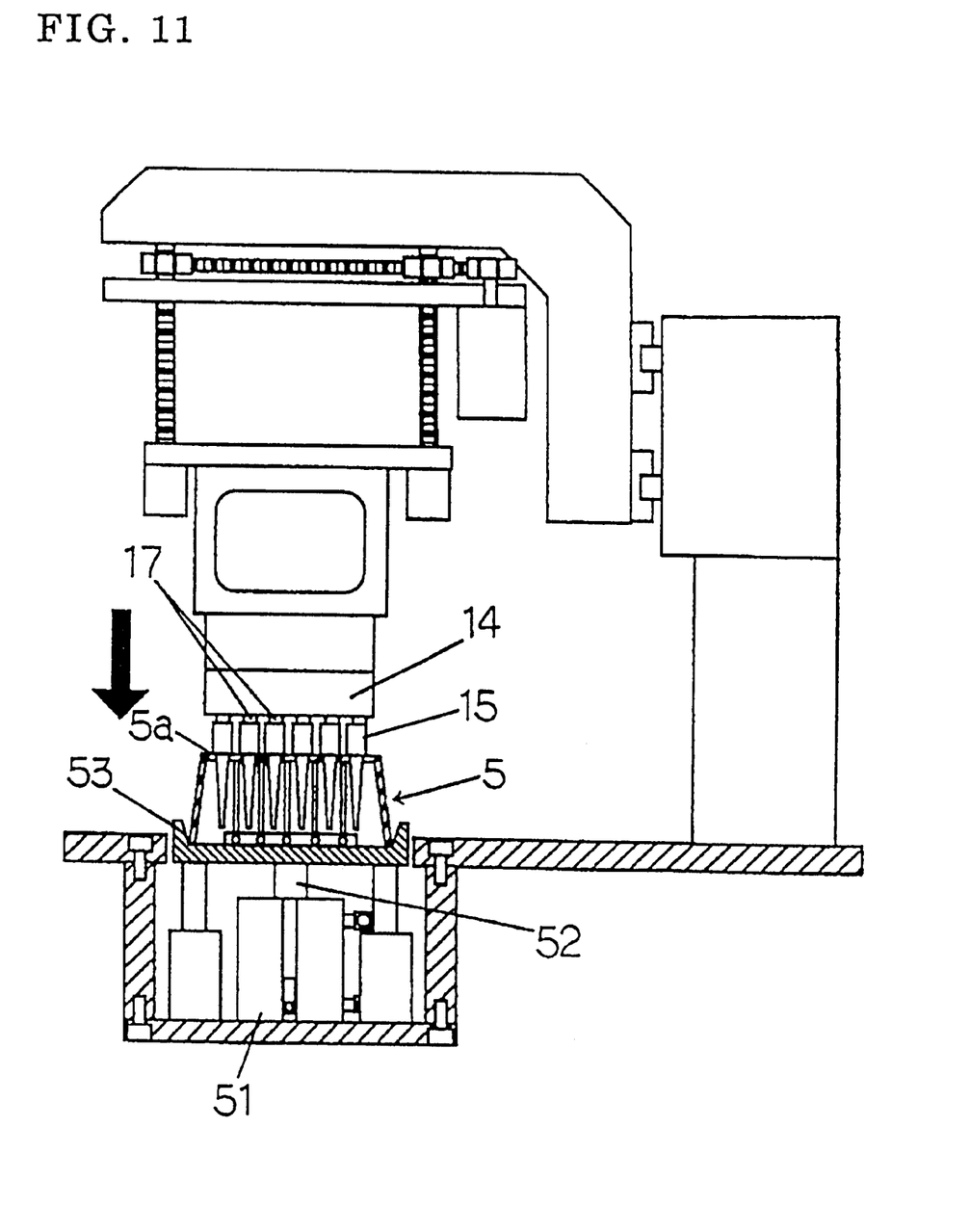
Figure 12:
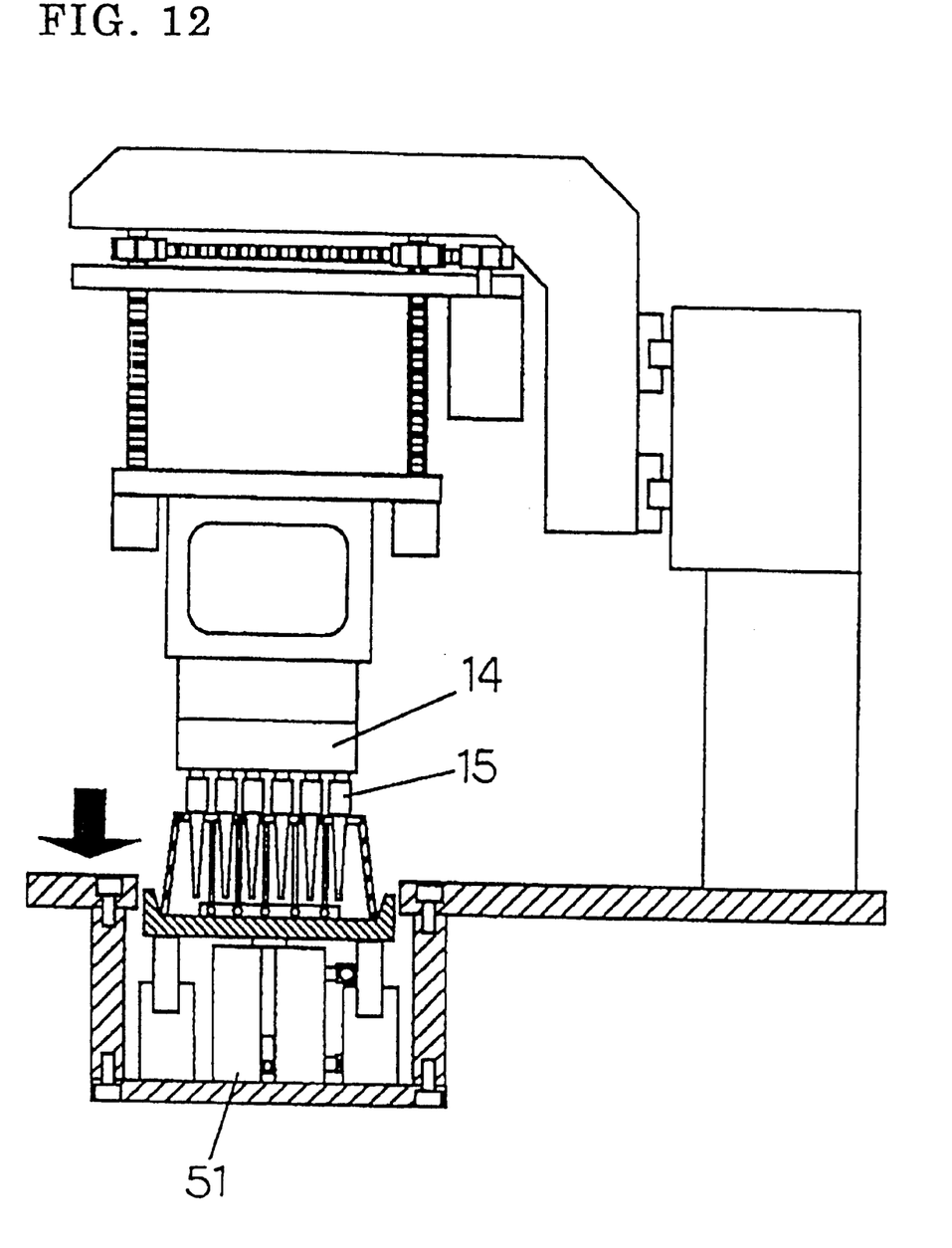

Then, a first distribution head 14, or the second distribution head 16, is carried to a place above the tip holder 5 (FIG. 10). The distribution head is then lowered relative to the tip holder 5 so that the nozzles 17 are fitted with a force in the top portions of the distribution tips 15 (FIG. 11, FIG. 12). If the first distribution head 14, or the second distribution head 16, is already fitted with distribution tips used in the previous distribution operation, these tips need to be detached at the tip detaching mechanism 19 prior to the fitting operation for new distribution tips.

FIG. 11 and FIG. 12 show how the distribution head 14 is lowered and the nozzles 17 are fitted with a force in the top portion of the tips 15. When the distribution head 14 is lowered, the nozzles 17 move into the distribution tips 15 at the top portions of their cylindrical shapes (FIG. 11). As either the nozzle 17 or the distribution tip 15 is made of a synthetic resin or other such material having a slight elasticity, the nozzle 17 can forcibly proceed into the top portion of distribution tip 15 to make an elastic fitting. The platform 53 is supported by the rod 52 of cylinder 51 with a thrusting force, and thus, further lowering of the distribution head 14 for a slight length, as illustrated in FIG. 12, makes the rod 52 retract downward against the thrust force of cylinder 51. In the meantime, the top portions of distribution tips 15 are surely fitted to the nozzles 17. As described earlier with reference to FIG. 7C, the pillars 55 support the top board 5a of tip holder 5 from its bottom surface for avoiding a downward deformation; therefore, the nozzles 17 can move surely into the top portions of distribution tips 15.

Figure 13:
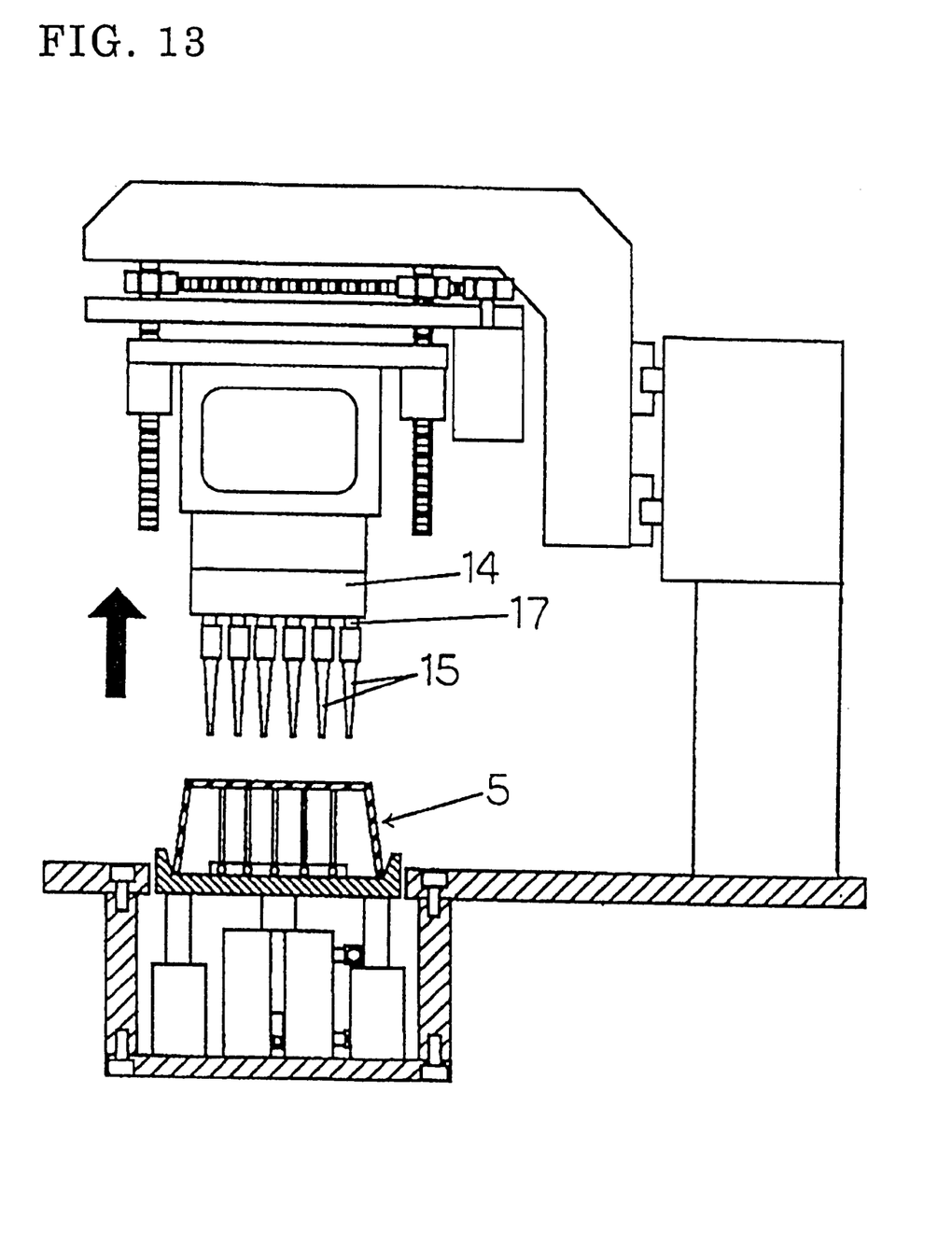

The distribution head 14 is lifted as illustrated in FIG. 13, and the distribution tips 15 fitted to the nozzles 17 follow together. Then, having been relieved from a load, the rod 52 of cylinder 51 comes up to the initial position. This completes the fitting operation for the distribution tips 15. The second distribution head 16 is fitted with the distribution tips 15 through the same procedure.

The number of distribution tips 15 to be attached to the first distribution head 14 is 30. When fitting the distribution tips 15 to the first distribution head 14, the cylinder 51 is connected with the regulator 62 of greater pressure, in order to support the platform 53 with a greater force from the bottom. The number of distribution tips 15 to be attached to the second distribution head 16 is 6. When fitting the distribution tips 15 to the second distribution head 16, the cylinder 51 is connected with the regulator 61 of smaller pressure, in order to support the platform 53 with a smaller force from the bottom.

Controlling the platform 53 supporting force in accordance with the number, type, etc. of distribution tips 15 to be attached to a distribution head contributes to providing an appropriate cushion force in the up and down direction when the distribution head comes down for the fitting of distribution tips 15 to nozzles 17. This ensures a sure fitting of a plurality of distribution tips 15 at once to a distribution head. This is also effective for preventing a possible breakage that could be caused on a distribution tip 15 at the insertion. Even if there is some error in the lowering stroke of a distribution head, it may be offset by the above-described cushion force. Although in the present embodiment two regulators 61 and 62 have been provided for switching the supporting force of cylinder 51 in two steps, viz. to the first distribution head 14 or to the second distribution head 16, the level of supporting force may be switched in any number of steps, or it may be controlled in analog mode.

While fitting operation of the distribution tips 15 is going on in one side, specimen plates 4C are taken out of the shelf board rows 34E, 34F of plate stocker 30 to be placed in the stages 10A, 10B; dilution plate 4A keeps dilution solution in the stage 10C; and medicine plate 4B in the stage 10D.

Figure 6:
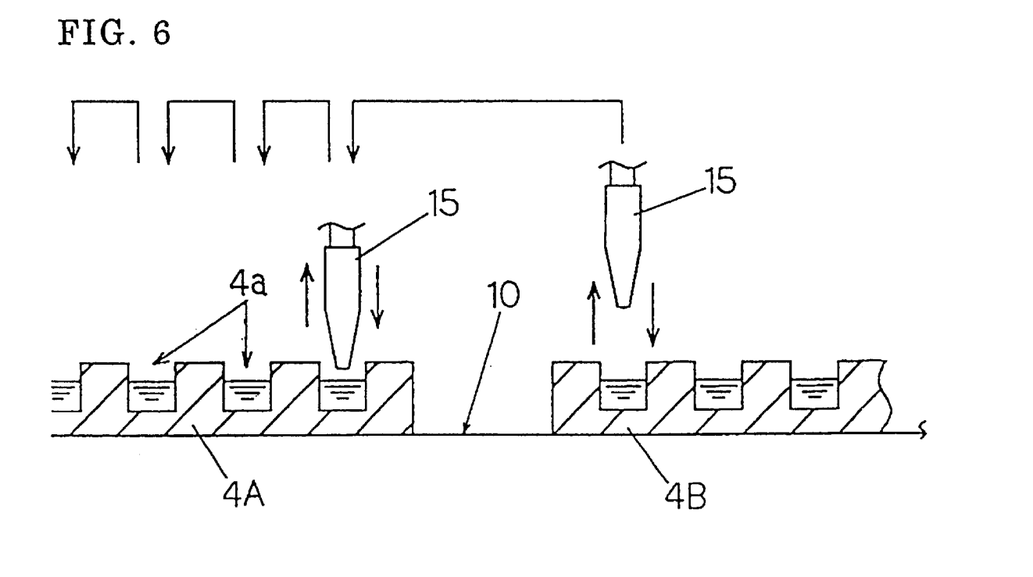
FIG. 6 is a cross sectional side view of plates in the distribution apparatus.

Next, referring to FIG. 6, description is made of an operation for providing a dilution system using the second distribution head 16. In the first place, the distribution tips 15 disposed in a line on the second distribution head 16 suck up medicine liquid from the medicine plate 4B placed on the stage 10D in a specified quantity, and then discharge the medicine liquid into the hollows 4a in the first row of the dilution plate 4A placed on the stage 10C, and stir the liquid within the hollows 4a. Thus the medicine liquid is mixed with a diluting solution already provided in the hollows 4a, and a medicine liquid diluted to a certain specific percentage is ready.

Then the distribution tips 15 of second distribution head 16 suck the diluted medicine liquid in a specified quantity, and discharge it into hollows 4a in the second row of the dilution plate 4A. Thus another diluted medicine liquid is offered, that is a further dilution of the diluted medicine liquid by a certain specific dilution index. Repeating the same operation provides a system of diluted liquids on a dilution plate 4A, where a medicine liquid diluted into various dilution indexes is disposed in respective rows.

The diluted liquids are transferred altogether in one operation to a specimen plate 10C placed in the stages 10A, 10B by the first distribution head 14. As the first distribution head 14 is provided with the distribution tips 15 disposed in correspondence with the arrangement of hollows 4a of plate 4, the diluted medicine liquids of various dilution indexes can be distributed at once.

Providing a first distribution head 14 and a second distribution head 16 which share the plate stage 10, on which a plurality of plates 4 can be placed, as a common field of operation enables performance of such operations as preparing diluted medicine liquids at different dilution indices (a dilution system) and distributing at once the dilution system to a specimen plate 4C on a single distribution stage 10. Conventionally, the above-described two kinds of operations were conducted in separate units of a distribution apparatus. A distribution apparatus in accordance with the present invention makes it possible to conduct these different kinds of operations in a single unit. Thus, the present automatic distribution apparatus contributes to space saving, as well as cost savings. Also, the concentration of various kinds of different operations on the same stage contributes to improving the operating efficiency.

The specimen plate 4C containing diluted liquids is taken by the transfer head 26 to be transferred out of the plate stage 10 to an incubator (not shown) or other experimental facilities. The specimen plate C after undergoing a certain scheduled process of experiments is received again by the transfer head 26, and placed on the waiting stage 12 awaiting a subsequent handling. The plate is then carried by second transfer means to the processing section C passing through the opening 3a.

The above-described handling process is described more in detail. Referring to FIG. 5, the waiting specimen plate 4C is once placed on the horizontal transfer arm 48, and then conveyed onto the vertical transfer arm 44 (arrow symbol "a"), lowered through the opening 3a (arrow symbol "b"), and eventually sent to an analyzer 40 (arrow symbol "c"). Among the specimen plates C which underwent certain scheduled analyzing operations, those which require further experimental procedure are carried again by the second transfer means to the distribution section A. The transfer head 26 transfers these plates to a certain specified shelf board 34 of the plate stocker 30 in stock section B, or to other experimental facilities.

The specimen plates 4C that have finished all the scheduled experiments are sent to a cleaner 41 disposed in the processing section C. The plates after cleaning are placed on a certain specified shelf board 34 of the plate stocker 30. As the distribution section A is located just above the processing section C within a single apparatus body, the transportation distance between the two sections is quite short and the time needed for the transportation is much shorter as compared with that needed in a conventional setup for automatic distribution. Thus the operating efficiency is significantly improved.

In the above exemplary mode of the embodiment, the first distribution head and the second distribution head have been provided, respectively, with a plurality of distribution tips in different arrangements, including a lattice arrangement and a line arrangement. However, it is not the intention of the present invention to limit the arrangement of distribution tips to the lattice form and the line form. The distribution tips may of course be disposed in any arrangements other than the lattice and the line. Furthermore, a plurality of distribution heads each having the same arrangement of distribution tips may be provided. Regardless of types of arrangement of the distribution tips in a distribution head, providing a plurality of distribution heads in a common distribution stage enables performance of different kinds of operations, which used to be conducted by plural units of a distribution apparatus, within a single unit of the distribution apparatus. Thus, a space-saving automatic distribution apparatus is presented at a low cost. Also, the concentrated operation of the various distributing processes in the same stage contributes to improving the operating efficiency.

As described in the foregoing, because a plurality of distribution heads have been provided to be available in a common distribution stage for performing different kinds of operations, an automatic distribution apparatus in accordance with the present invention is capable of carrying out different kinds of operations, which conventionally required plural units of separate distribution apparatus. In this way, the present invention contributes to the saving of space of the apparatus and the cost. In addition, the concentrated operation significantly improves efficiency of the distributing operations. Furthermore, by providing a first distribution head with a plurality of distribution tips disposed in a lattice arrangement and a second distribution head with a plurality of distribution tips disposed in a line arrangement, such operations as preparation of a dilution system of a medicine liquid and distribution at once of diluted medicine liquids to a specimen plate can be conducted on a single distribution stage. Thus, the efficiency of distribution operations, in which different distribution heads are needed, can be significantly improved.

Although in the above exemplary embodiment an air cylinder has been used for the thrust means, a hydraulic cylinder or an air-hydro cylinder may of course be used instead. However, in view of the total performance including function, cost and ease of maintenance, the air cylinder seems to be the most preferred thrusting means.

What is claimed is:

1. An automatic distribution apparatus comprising:
    a distribution head having a plurality of nozzles designed to be detachably provided at respective bottom ends with tips for sucking liquid samples;
    a tip exchange stage on which a tip holder for holding a plurality of unused tips upright is placed; and
    a moving device for moving said distribution head up and down relative to the tip holder placed on said tip exchange stage so that the bottom ends of said nozzles are inserted in the tips held on the tip holder,
    wherein said tip exchange stage is equipped with a platform for holding said tip holder, an air cylinder for thrusting the platform upward, and a pressure regulator for controlling a thrusting force of the air cylinder by regulating pressure of air in said air cylinder.

2. The automatic distribution apparatus of claim 1, wherein said pressure regulator controls the thrusting force in accordance with total number of tips to be fitted in one operation.

3. The automatic distribution apparatus of claim 1, wherein said pressure regulator controls the thrusting force in accordance with type of tips to be fitted.

4. The automatic distribution apparatus of claim 1, wherein
    the tip holder comprises a horizontal top board provided with a plurality of holes for accepting and holding tips and a foot extending downward from the top board, and
    said platform is provided with a support member for supporting the top board by making contact from a bottom surface of the top board.

5. The automatic distribution apparatus of claim 4, wherein said support member comprises a plurality of pins.

6. An automatic distribution apparatus comprising:
    a first distribution head having a plurality of nozzles designed to be detachably provided at respective bottom ends with tips for sucking liquid samples;
    a second distribution head having nozzles fewer in number than said nozzles of said first distribution head;
    a tip exchange stage on which a tip holder for holding a plurality of unused tips upright is placed;
    a first moving device for moving said first distribution head up and down relative to the tip holder placed on said tip exchange stage so that the bottom ends of respective ones of said nozzles are inserted in the tips held on the tip holder; and
    a second moving device for moving said second distribution head up and down relative to the tip holder placed on said tip exchange stage so that the bottom ends of respective ones of said nozzles are inserted in the tips held on the tip holder,
    wherein said tip exchange stage is equipped with a platform for holding said tip holder, an air cylinder for thrusting the platform upward, and a pressure regulator for controlling a thrusting force of the air cylinder by regulating pressure of air in said air cylinder.

7. The automatic distribution apparatus of claim 6, wherein said pressure regulator controls the thrusting force to be greater for inserting the nozzles of said first distribution head into tips than for inserting the nozzles of said second distribution head into tips.

8. The automatic distribution apparatus of claim 6, wherein
    the tip holder comprises a horizontal top board provided with a plurality of holes for accepting and holding tips and a foot extending downward from the top board, and
    said platform is provided with a support member for supporting the top board by making contact from a bottom surface of the top board.

9. The automatic distribution apparatus of claim 8, wherein said support member comprises a plurality of pins.

* * * * *